US012667551B2

(12) United States Patent (10) Patent No.: US 12,667,551 B2
Kawarasaki et al. (45) Date of Patent: Jun. 30, 2026

(54) RENAL FUNCTION MAINTENANCE AND PROTECTION AGENT, AND METHOD FOR EVALUATING EFFECT THEREOF

(71) Applicant: MARUHA NICHIRO CORPORATION, Tokyo (JP)

(72) Inventors: Masataka Kawarasaki, Tokyo (JP); Yosuke Chiba, Tokyo (JP); Akira Kamata, Tokyo (JP); Tomoaki Hashimoto, Tokyo (JP); Yoichiro Shirahama, Tokyo (JP)

(73) Assignee: MARUHA NICHIRO CORPORATION, Tokyo (JP)

( * ) Notice: Subject to any disclaimer, the term of this patent is extended or adjusted under 35 U.S.C. 154(b) by 1172 days.

(21) Appl. No.: 17/254,256

(22) PCT Filed: Jul. 19, 2019

(86) PCT No.: PCT/IB2019/056185
§ 371 (c)(1),
(2) Date: Dec. 18, 2020

(87) PCT Pub. No.: WO2019/244140
PCT Pub. Date: Dec. 26, 2019

(65) Prior Publication Data
US 2021/0275486 A1 Sep. 9, 2021

(30) Foreign Application Priority Data
Jun. 21, 2018 (JP) ................................. 2018-118020
Jun. 20, 2019 (JP) ................................. 2019-114799

(51) Int. Cl.
| | |
|---|---|
| A61K 31/202 | (2006.01) |
| A23K 20/158 | (2016.01) |
| A23L 33/00 | (2016.01) |
| A23L 33/12 | (2016.01) |
| A61K 9/00 | (2006.01) |
| A61P 13/12 | (2006.01) |
| G01N 33/68 | (2006.01) |

(52) U.S. Cl.
CPC .......... *A61K 31/202* (2013.01); *A23K 20/158* (2016.05); *A23L 33/12* (2016.08); *A23L 33/40* (2016.08); *A61K 9/0053* (2013.01); *A61K 9/0056* (2013.01); *A61P 13/12* (2018.01); *G01N 33/6812* (2013.01); *A23V 2002/00* (2013.01); *G01N 2800/52* (2013.01)

(58) Field of Classification Search
CPC ..... A61K 31/202; A23K 20/158; A61P 13/12; A23V 2002/00
See application file for complete search history.

(56) References Cited

U.S. PATENT DOCUMENTS

| | | | |
|---|---|---|---|
| 5,059,622 A | 10/1991 | Sears | |
| 2013/0157252 A1* | 6/2013 | Sato ................... | G01N 33/6806 |
| | | | 562/561 |
| 2016/0091494 A1* | 3/2016 | Taylor-Robinson ........................ | |
| | | | G01N 33/57438 |
| | | | 435/7.1 |

FOREIGN PATENT DOCUMENTS

| | | | |
|---|---|---|---|
| JP | 02235811 A | * | 9/1990 |
| JP | 7-267898 A | | 10/1995 |
| JP | 9-87176 A | | 3/1997 |
| JP | 2002-345452 A | | 12/2002 |
| JP | 2012-112784 A | | 6/2012 |
| JP | 2016-14685 A | | 1/2016 |
| WO | WO 99/29316 A1 | | 6/1999 |
| WO | WO 2011/136228 A1 | | 11/2011 |
| WO | WO 2016/152054 A1 | | 9/2016 |

OTHER PUBLICATIONS

Moriyama et al. "The Renoprotective Effects of Docosahexaenoic Acid as an Add-on Therapy in Patients Receiving Eicosapentaenoic Acid as Treatment for IgA Nephropathy: A Pilot Uncontrolled Trial", Internal Medicine, Nov. 2017, pp. 173-179. https://www.jstage.jst.go.jp/article/internalmedicine/57/ (Year: 2017).*
Nakamura et al. Effects of Tridocosahexaenoyl-Glycerol Emulsion on Proteinuria in Rats with Nephrotoxic Serum Nephritis, Nephron Extra, Oct. 2011 (Year: 2011).*
Marze et al. In vitro digestion of fish oils rich in n-3 polyunsaturated fatty acids studied in emulsion and at the oil-water interface, Food & Function, Oct. 2012, pp. 231-239. (Year: 2012).*
Hobbs, Dietary Fish Oil Prevents the Development of Renalhypertensive Ratsdamage in Salt-Loaded Stroke-Prone Spontaneously, Clinical Experimental and Physiology, Jan. 1996, pp. 508-513 (Year: 1996).*
JPH 02235811A Machine Translation (Year: 1990).*
Chapman et al. Hypertension in Autosomal Dominant Polycystic Kidney Disease, Adv Chronic Kidney Dis, Mar. 2010, pp. 153-163. (Year: 2010).*
JP 02235811 Machine translation (Year: 1990).*
JP-02235811 A Machine translation (Year: 1990).*
Miyazaki, et al., "Dietary docosahexaenoic acid ameliorates, but rapeseed oil and safflower oil accelerate renal injury in stroke-prone spontaneously hypertensive rats as compared with soybean oil, which is associated with expression for renal transforming growth factor-β, fibronectin and renin," Biochimica et Biophysica Acta, vol. 1483, pp. 101-110 (2000).

(Continued)

*Primary Examiner* — Sarah Pihonak
*Assistant Examiner* — Mikhail O'Donnel Robinson
(74) *Attorney, Agent, or Firm* — Foley & Lardner LLP

(57) ABSTRACT

Provided is a renal function maintenance and protection agent comprising as an active ingredient of a triglyceride of docosahexaenoic acid (DHA) or eicosapentaenoic acid (EPA) or a mixture of a triglyceride of docosahexaenoic acid (DHA) and a triglyceride of eicosapentaenoic acid (EPA), which can be used as a pharmaceutical or food composition. A triglyceride of docosahexaenoic acid (DHA) or eicosapentaenoic acid (EPA) or a mixture of a triglyceride of docosahexaenoic acid (DHA) and a triglyceride of eicosapentaenoic acid (EPA) is used as an active ingredient for renal function maintenance and protection agents.

1 Claim, 6 Drawing Sheets

(56)           References Cited

OTHER PUBLICATIONS

Hobbs, et al., "Dietary Fish Oil Prevents the Development of Renal Damage in Salt-Loaded Stroke-Prone Spontaneously Hypertensive Rats," *Clinical and Experimental Pharmacology and Physiology*, vol. 23, pp. 508-513 (1996).
Schuchardt, et al., "Bioavailability of Long-Chain Omega-3 Fatty Acids," *Prostaglandins, Leukotrienes and Essential Fatty Acids*, vol. 89, pp. 1-8 (2013).
Hajime, et al., "Development of Continued Pharmaceutical— Efficacy in nonclinical (preclinical) Studies," 24 pages (1991).
Banno, et al., "Lymphatic absorption of docosahexaenoic acid given as monoglyceride, diglyceride, triglyceride, and ethyl ester in rats," *J Nutr Sci Vitaminol*, vol. 48, 1 page (2005).
International Search Report issued in International Patent Application No. PCT/IB2019/056185, completed Sep. 27, 2019.
Supplemental Partial European Search Report issued in European Patent Application No. 19821742, completed Sep. 2, 2022.
Communication issued in European Patent Application No. 19821742. 4, dated Mar. 13, 2026.

* cited by examiner

[Fig.1]
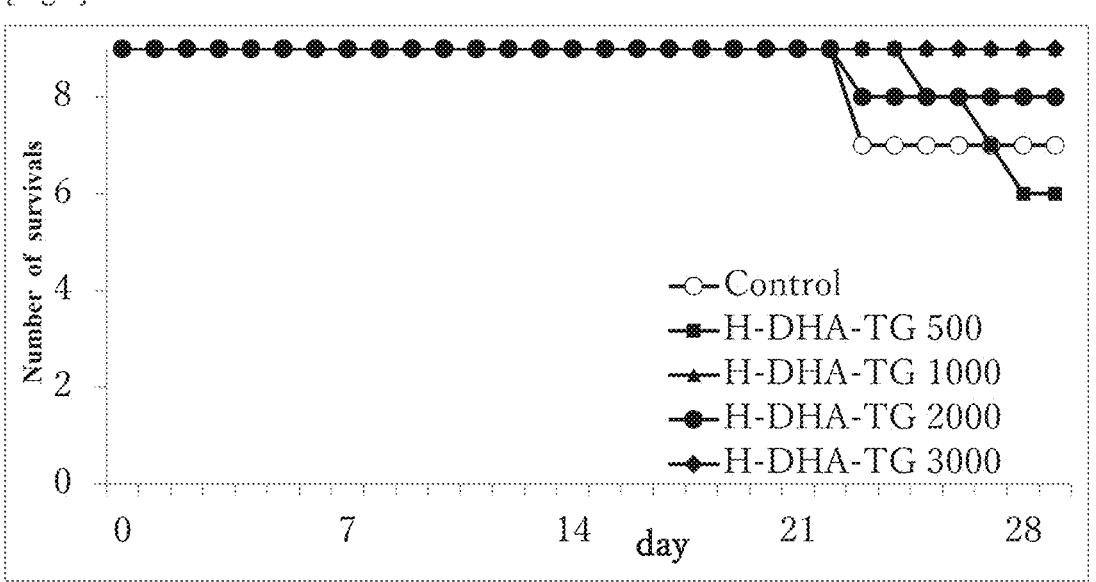
[Fig. 2]
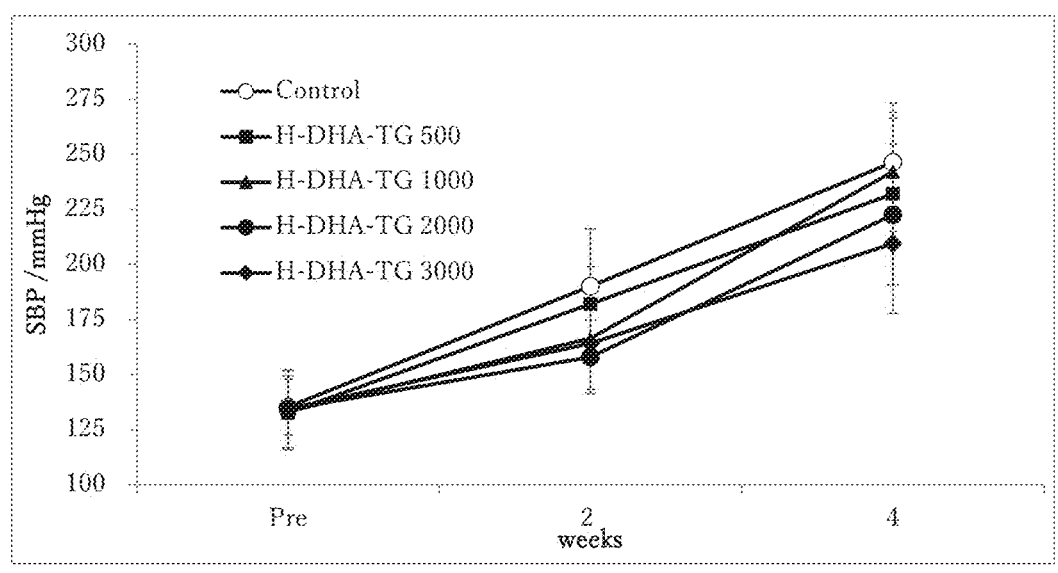

[Fig. 3]
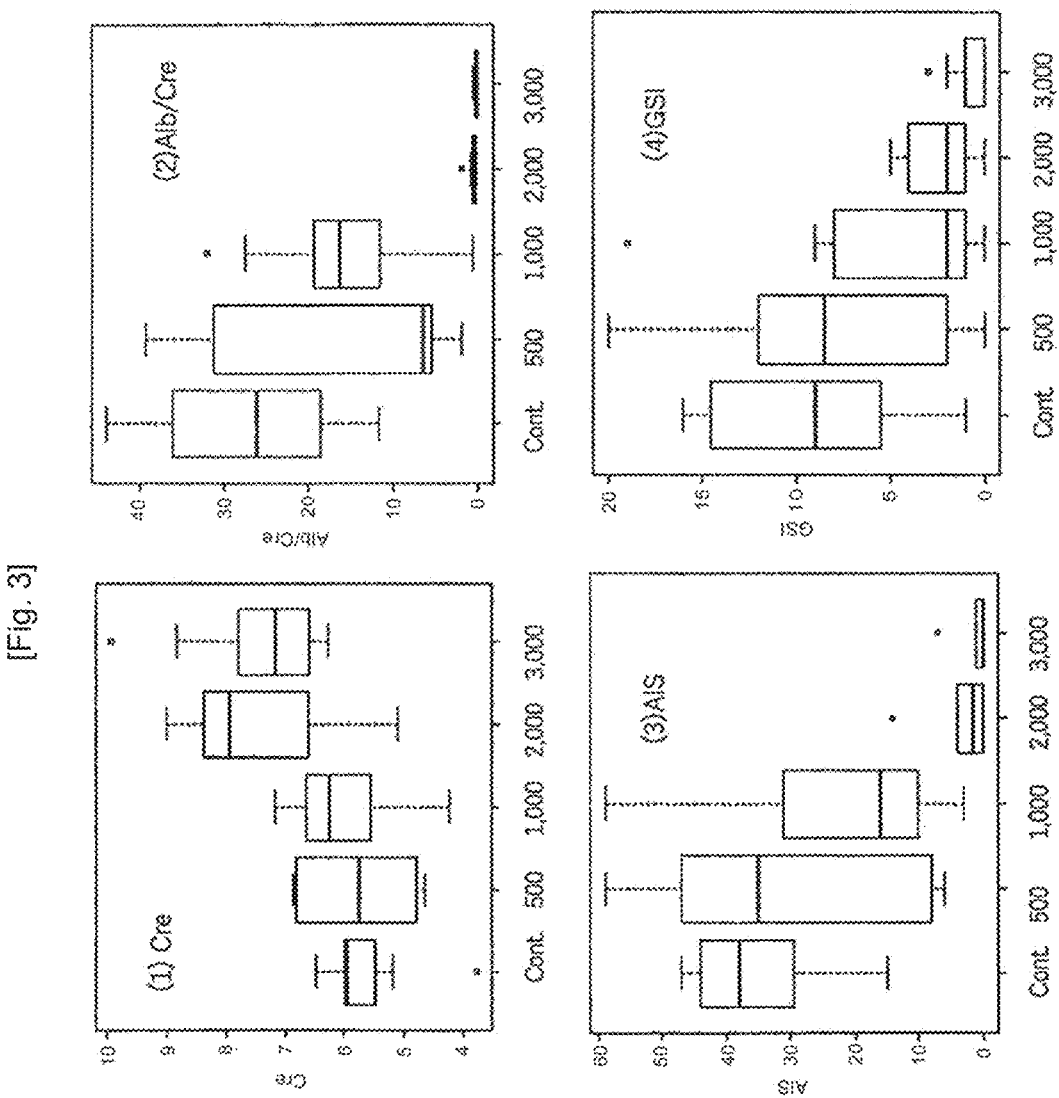

[Fig. 4]
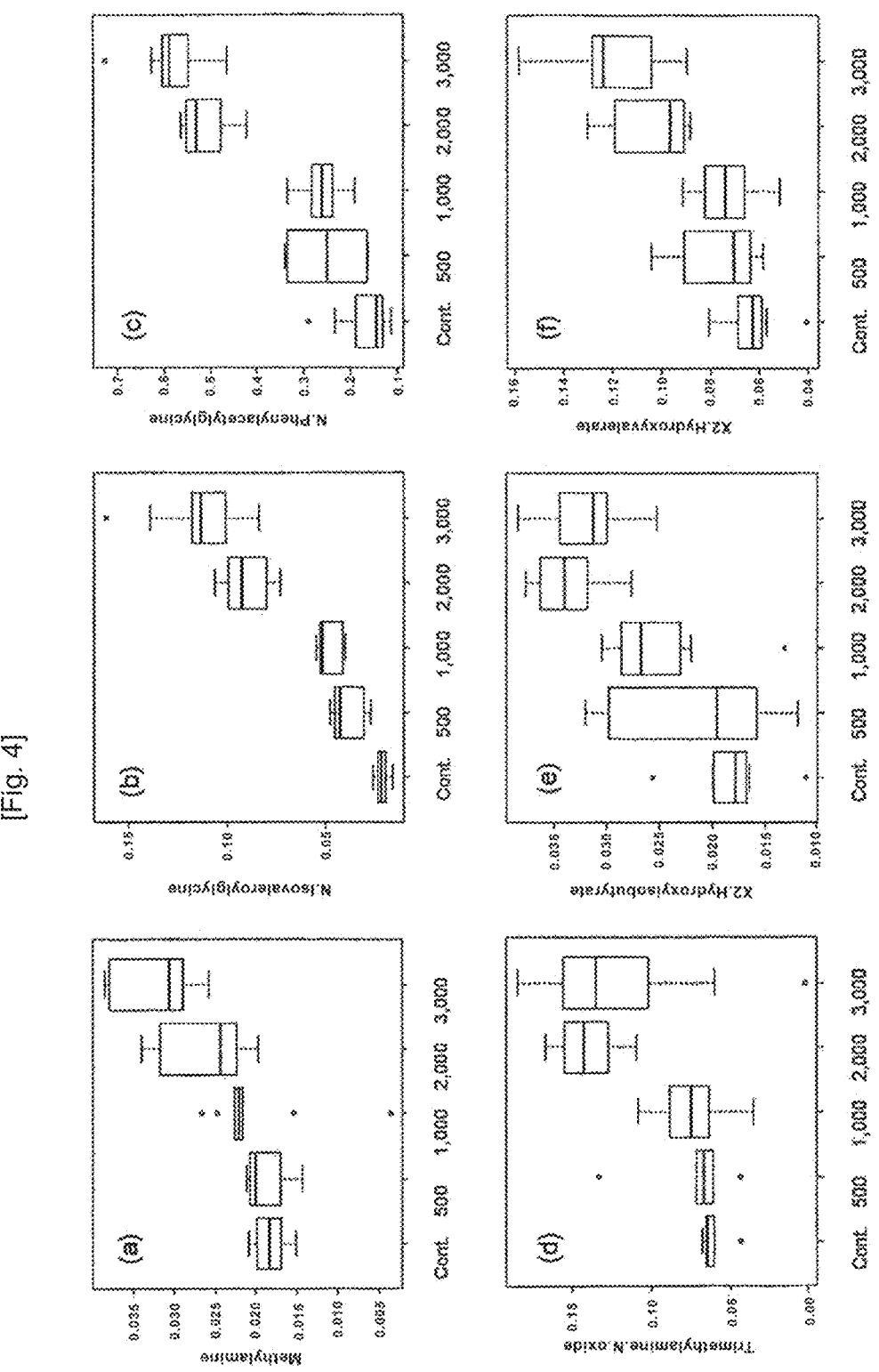

[Fig. 5]
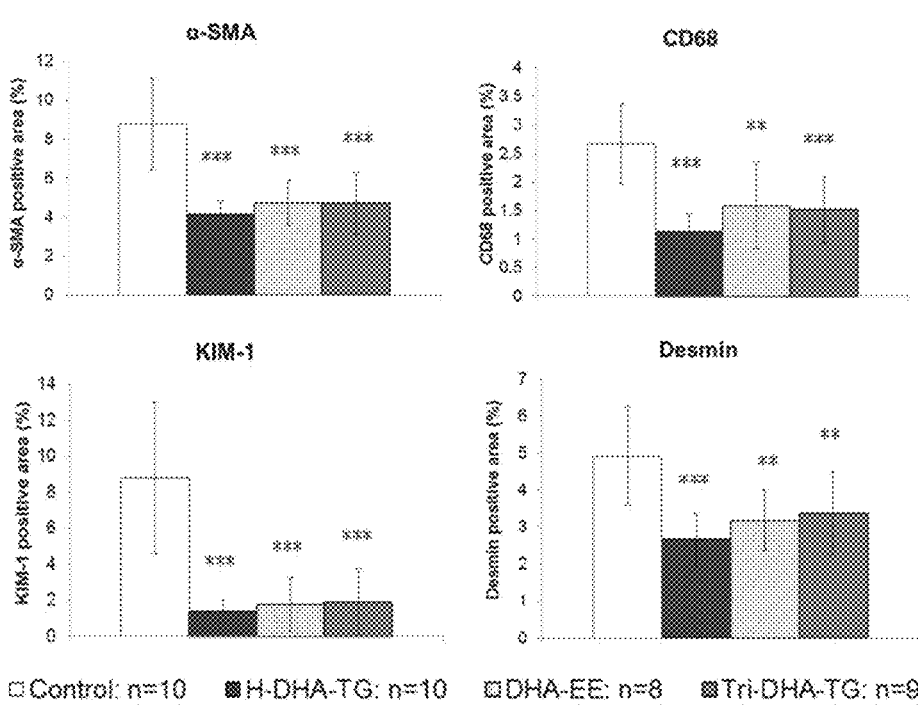
Dunnett test: vs. Control: $*p<0.05$, $p<0.01$, $*p<0.001$

[Fig. 6]
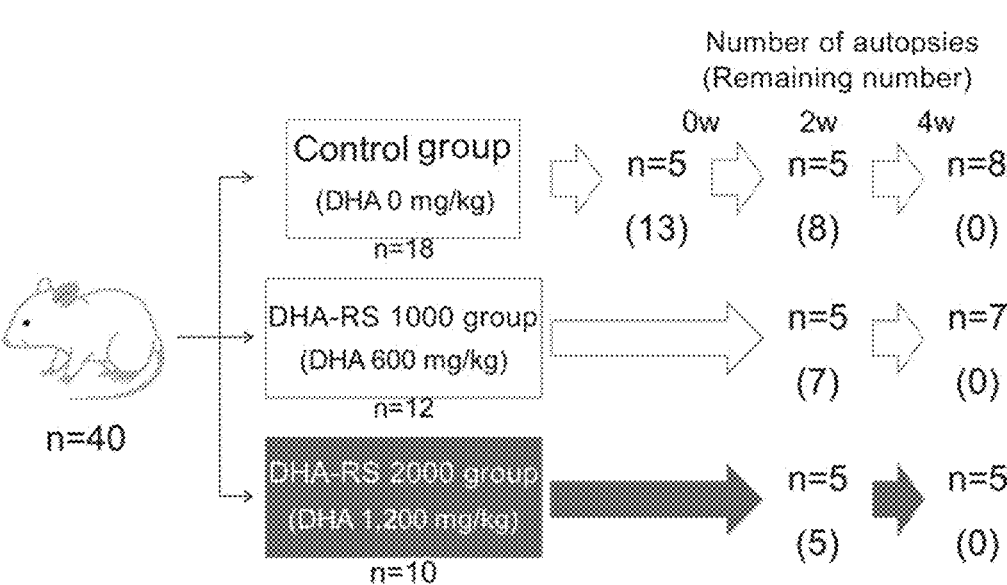
※ Control group: 6 animals died at 4 weeks, and the final 2 animals.

[Fig. 7]
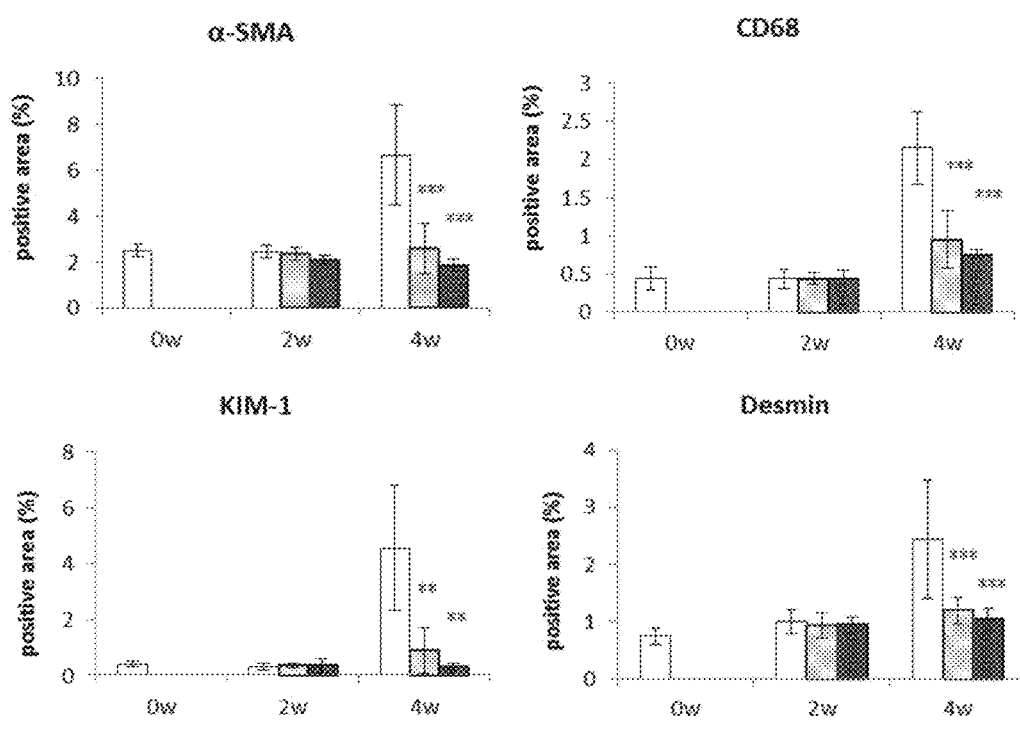
☐Control ▨H-DHA-TG:1,000mg/kg ■H-DHA-TG:2,000mg/kg
Dunnett test: vs. Control:  *p<0.05, p<0.01, *p<0.001

RENAL FUNCTION MAINTENANCE AND PROTECTION AGENT, AND METHOD FOR EVALUATING EFFECT THEREOF

CROSS-REFERENCE TO RELATED APPLICATIONS

This application is the U.S. National Stage of International Patent Application No. PCT/IB2019/056185, filed Jul. 19, 2019, which claims priority to Japanese Patent Application No. 2018-118020, filed Jun. 21, 2018, and Japanese Patent Application No. 2019-114799, filed Jun. 20, 2019. The contents of these applications are incorporated herein by reference in their entireties.

TECHNICAL FIELD

The present invention relates to a renal function maintenance and protection agent, and a method for evaluating the effect thereof.

TECHNICAL BACKGROUND

The kidneys are organs that filter the blood, reabsorb the required proteins and carbohydrates, and excrete waste products as urine.

Specifically, blood is filtered by the renal glomeruli, and the required carbohydrates and minerals are reabsorbed by the renal tubules.

When the renal glomerulus ruptures, protein leaks into the urine and it does not regenerate.

And, when the renal tubule ruptures, the waste product does not excrete, and it is forced to shift to dialysis or kidney transplantation.

The antihypertensive agents ACE-inhibitor, AT1 receptor antagonist, and Ca-antagonist are considered to be effective in protecting renal function.

Patent Document 1 discloses the inhibitory effect of administration of docosahexaenoic acid on the reduction of glomerular function-renal function in glomerulonephritis model rats in which antigen-antibody complexes containing rabbit serum albumin (RSA) as an antigen were generated into the body.

Non-Patent Documents 1 and 2 disclosed that renal function was protected by administration of ethyl esters of docosahexaenoic acid (DHA-EE) or ethyl esters of eicosapentaenoic acid (EPA-EE) to salt-sensitive spontaneously hypertensive stroke-prone rats.

As pharmaceuticals, these high-purity ethyl esters are utilized in Japan within the range of prescription by a physician, and it is not common to utilize ethyl esters as pharmaceuticals for prophylactic ingestion outside of a pharmaceutical prescription.

On the other hand, there is a description in Non-Patent Document 3 that a simple bioabsorbable property in an n–3 based polyunsaturated fatty acid is better in triglycerides than ethyl esters.

On the other hand, Non-Patent Document 4 discloses that when triglycerides of DHA (DHA-TAG), DHA-EE, or triglycerides of EPA (EPA-TAG) and EPA-EE were administered, DHA-TAG and DHA-EE lowered blood glucose levels to the same extent as control, and no effect was observed in EPA-TAG and EPA-EE.

Therefore, it is desirable from the viewpoint of the health contribution of the public if the renal function preventive effect can be recognized by the triglycerides (TAG) mainly containing DHA, which is mainly contained in polyunsaturated fatty acid contain lipids, particularly fish oil and the like.

When extrapolating from laboratory animals (rats) to large animals or humans, metabolic activity in each species should be considered.

For example, when extrapolating the results of animal studies to humans, it is generally known for pharmacokinetics that the dose in animal studies (mg/kg) is replaced by (mg/body) in humans (non-Patent Document 5), which provides a reference for setting human clinical doses.

PRIOR-ART DOCUMENT

Patent Document

Patent document 1: JPH9-87176

Non-Patent Document

Non-patent document 1. Biochimica et Biophysica Acta, 2000,1483,101-110

Non-patent document 2: Clin.Exp.Pharmacol. Physiol., 1996,23,508-513

Non-patent document 3: Prostagland.leukotriene Essential Fatty Acid,2013,89,1

Non-patent document 4: FOOD ANALYSIS TECHNOLOGY CENTER, Mail Magazine, Issued in October 2015, vol. 115, "Structure and function of n–3 based polyunsaturated fatty acid binding lipids," Graduate School of Fisheries Science. Hokkaido University, Masashi Hosokawa, Associate Professor, http://www.mac.or.jp/mail/151001/02.shtml (FIG. 3)

Non-patent document 5: Development of Continued Pharmaceutical, 1991, Vol. 8, pp. 7-18, Hirokawa Shoten

SUMMARY OF THE INVENTION

Problems to be Solved by the Present Invention

It is an object of the present invention to provide a renal function maintenance and protection agent comprising as an active ingredient of a triglyceride of docosahexaenoic acid (DHA) or eicosapentaenoic acid (EPA) or a mixture of a triglyceride of docosahexaenoic acid (DHA) and a triglyceride of eicosapentaenoic acid (EPA), which can be used as a pharmaceutical or food composition.

Means for Solving the Problems

The renal function maintenance and protection agent according to the present invention is characterized in that it comprises a triglyceride of docosahexaenoic acid (DHA) or eicosapentaenoic acid (EPA) (DHA-TG) (EPA-TO) or a mixture of a triglyceride of docosahexaenoic acid (DHA) (DHA-TG) and a triglyceride of eicosapentaenoic acid (EPA) (EPA-TG) as an active ingredient for maintenance and protection of renal function.

The method of use a single substance of DHA-TG or EPA-TG or a mixture of DHA-TG and EPA-TG according to the present invention is characterized by the use of a single substance of DHA-TG or EPA-TG or a mixture of DHA-TG and EPA-TG as an active ingredient for renal function maintenance and protection in the production of renal function maintenance and protective agents.

The renal function maintenance and protection agent according to the present invention can be used as a pharmaceutical use or as a food composition.

The effect of the renal function maintenance and protection agent according to the present invention can be evaluated by the following evaluation method.

In other words, the method for evaluating an effect of administration of the renal function maintenance and protection agent according to the present invention, to an administration target, characterized by using at least one of the following indices A and B:

Index A:

A concentration of N-acylated glycine metabolites (in creatinine equivalents) and/or niacinamide metabolites (in creatinine equivalents) in urine collected from the administration target, Index B:

A concentration of at least one selected from 2-aminopimeric acid, 2-hydroxybutyric acid, citric acid, glycolic acid, phenylacetic acid and niacinamide in serum collected from the administration target.

Effect of Invention

According to the present invention, it is possible to provide a renal function maintenance and protection agent comprising a single substance of DHA-TG or EPA-TG, or a mixture of DHA-TG and EPA-TG as an active ingredient that can be used as a pharmaceutical or food composition.

BRIEF DESCRIPTION OF THE DRAWINGS

FIG. 1 is a diagram showing the results of examining the effects of administration of DHA highly concentrated triglyceride (H-DHA-TG) on spontaneously hypertensive stroke-prone rats (SHR-SP/Izm) by the number of survivors.

FIG. 2 is a diagram showing the results of examining the effect of administration of H-DHA-TG on blood pressure in spontaneously hypertensive stroke-prone rats (SHR-SP/Izm).

FIG. 3 is a diagram showing the fluctuation results of urinary creatinine (Cre) concentration, urinary albumin/creatinine ratio (Alb/Cre), glomerulosclerosis score (OSI), and renal artery injury score (AIS) in spontaneously hypertensive stroke-prone rats (SHR-SP/Izm) due to administration of HDA-TG.

FIG. 4 is a diagram showing the fluctuation results of the concentration (creatinine equivalents) of urinary metabolites, i.e., (a) methylamine, (b) N-isovaleroviglycine, (c) N-phenylacetylglycine. (d) trimethylamine-N-oxide, (e) 2-hydroxyisobutyrate, and (f) 2-hydroxyvalarate [units represent respective metabolite levels (μM)/Cre (μM)], in spontaneously hypertensive stroke-prone rats (SHR-SP/Izm) due to administration of HDA-TG.

FIG. 5 is a diagram showing the results of α-SMA, CD68, KIM-1 and Desmin immunostaining images and positive area (%) of renal tissue obtained in Example 3.

FIG. 6 is a diagram for explaining the experimental scheme used for examining the mechanism of action and metabolite dynamics of H-DHA-TG.

FIG. 7 is a diagram showing the results of α-SMA, CD68, KIM-1 and Desmin immunostaining images and positive area (%) of renal tissue obtained in Example 4.

DETAILED DESCRIPTION OF THE PRESENT INVENTION

Non-Patent Document 3 generally describes that a simple bioabsorbability in an n−3 based polyunsaturated fatty acid is better for triacylglycerol (TAG, triglyceride) than EE.

However, as disclosed in non-patent document 4, when DHA-TAG, DHA-EE, or EPA-TAG, EPA-EE are administered to diabetic disease model animals, for example, DHA-TAG, DHA-EE lowers blood glucose levels to the same extent as control, and EPA-TAG, EPA-EE have not shown any effect.

In other words, in DHA and EPA, bioabsorbability is not directly reflected in the effect of bioactivity, and the difference in bioactivity between these triglycerides and ethyl esters is still unclear.

Patent Document 1 describes that DHA and a salt, ester or amide thereof can be utilized as an active ingredient of a glomerulonephritis inhibitor.

In an example of Patent Document 1, the administration of DHA to a model rat in which glomerulonephritis induced by RSA-induced generation of antigen-antibody complexes inhibited the decrease in glomerular function-renal function, as determined by measurement results of the urinary protein concentration as an index of decreased renal function, urinary creatinine concentration and blood creatinine concentration as an index of glomerular function.

However, Patent Document 1 has not been validated for the suppressive effect of DHA of esters and amides on the reduction of glomerular function-renal function Therefore, from Patent Document 1, it is difficult to conceive a renal function maintenance and protective effect by administration of an ester body of DHA The present inventors examined the use of n−3 based polyunsaturated fatty acids such as DHA and EPA as active ingredients for maintaining renal function and protecting renal function, and clarified the point of action of n−3 based polyunsaturated fatty acids on the kidneys.

It was concluded that it is important to identify the time point at which the effect after administration to the administration targets can be predicted.

As a result of various studies based on such conclusions, the present inventor discovered a novel biomarker for evaluating renal function maintenance and renal function protective effect, and based on the results of evaluation on the effect by such biomarker, it was concluded that n−3 based polyunsaturated fatty acids such as DHA and EPA have renal function maintenance and renal function protective effect.

In addition, with respect to the point of action of n−3 based polyunsaturated fatty acids on the kidney, non-Patent Document 1 captures the entire lesion of the renal glomerulus, but does not discuss the details of its point of action.

Regarding biomarkers for evaluating the effects of n−3 based polyunsaturated fatty acids, in Patent Document. 1, urinary proteins as an index of decreased renal function and urinary and blood creatinine as an index of glomerular function are used.

In non-Patent Document 1, the expression levels of TGF-b, Fibronectin and Renin by systolic blood pressure, urinary protein, blood urea nitrogen (BUN), and renal mRNA are used; in non-Patent Document 2, urinary protein levels are used.

These conventional biomarkers are indicative of reduced, abnormal, or possibly occurring renal function and can be used to assess therapeutic or preventive effects.

However, it cannot be utilized as a biomarker for which time after administration of n−3-based polyunsaturated fatty acids or, in what circumstances, n−3-based polyunsaturated fatty acids act.

That is, there is still an unknown situation about such biomarkers.

According to our examination, the effects of renal function maintenance and protection agents in the present invention were found to include effects due to fibrosis inhibition (alpha-smooth muscle actin: α-SMA), inflammation inhibition (CD68), spheroid podocyte (podocyte) injury inhibition (Desmin) and proximal tubule injury inhibition (Kim-1) by immunostaining observations of renal pathology.

A method for evaluating the effect of a renal function maintenance and a protective agent containing an n–3 based polyunsaturated fatty acid as an active ingredient using a biomarker newly found by the present inventor is characterized in that at least one of the following indices A and B is used.

Index A:

A concentration of N-acylated glycine metabolites (in creatinine equivalents) and/or niacinamide metabolites (in creatinine equivalents) in urine collected from the administration target, Index B:

A concentration of at least one selected from 2-aminopimeric acid, 2-hydroxybutyric acid, citric acid, glycolic acid, phenylacetic acid and niacinamide in serum collected from the administration target.

One of the indices A and B may be used to evaluate the effect, or both of these indices may be used to evaluate the effect.

In the method for evaluating an effect according to the present invention, it is possible to evaluate an effect of an n–3 based polyunsaturated fatty acid by grasping a kinetics of an in vivo metabolite based on administration of an n–3 based polyunsaturated fatty acid using at least one of indices A and B described above.

The biomarkers N-acylated glycine metabolites in index A may include N-4-hydroxyphenylacetylglycine, N-phenylacetylglutamine, N-phenylacetylglycine and N-isovaleroylglycine. At least one of these can be used as the index A.

Among these, it is preferable to select N-phenylacetylglycine and/or N-isovaleroylglycine.

In addition, examples of the niacinamide metabolite which is a biomarker in the index A include 1-methylnicotinamide, nicotinamide N-oxide, and nicotiurate.

At least one of these can be used as the index A.

Whether urinary concentrations of these biomarkers before or after administration to administration targets vary with the administration of n–3 based polyunsaturated fatty acids can assess the effects of n–3 based polyunsaturated fatty acids For variations in urinary concentrations of this biomarker, it is preferable to use an increase due to administration in the value of the pre-dose or non-dose level to the administration targets Furthermore, this increase is preferably at least 1.2 times (more than 1.2 times) greater than that before or without administration. If this increase is more than 1.2 times, it can be more reliably predicted or confirmed that the intended effect will be obtained.

The effect of n–3 based polyunsaturated fatty acids can be assessed depending on whether concentrations of each biomarker of index B in serum before or after administration to administration targets vary with the administration of n–3 based polyunsaturated fatty acids.

As variations of concentrations in serum of these biomarkers, variations due to administration in the value of the pre-dose or non-dose to the administration targets, should preferably be used.

In addition, it is preferable that this variation lies at one of the following levels (B/A times: A: the value of the pre-dose or non-dose to the administration targets; B: values varied with administration).

(1) 2-Aminopimelic acid: not more than 0.8 times, (2) 2-Hydroxybutyric acid: not more than 0.6 times, (3) Citric acid: 0.85 times or less, (4) Glucolic acid: not more than 0.80 times and (5) Phenylacetic acid: not more than 0.2 times, (6) Niacinamide (niacinamide): 1.4 times or more.

One level of variation in any of the above (1) to (6) can predict or confirm that the intended effect will be obtained.

More specifically, all levels of variation (1) to (6) above can be more reliably predicted or confirmed to provide the desired effect.

A set for evaluation of an effect can be formed by combining a reference standard of at least one of a biomarker for an index A and a biomarker for an index B described above with an instruction describing an evaluation method and an evaluation criterion described above.

An analytical equipment (e.g., a nuclear magnetic resonance instrument (NMR), gas chromatography (GC), high performance chromatography (HPLC), mass spectrometry instrument (MS), or the like) or an analytical instrument for identification and quantitation of each biomarker may be combined in this set.

In addition, instructions for evaluation methods and criteria may be available from websites on the net.

By using the method for evaluating the effect according to the present invention, it is possible to confirm the target effect by administration of the n–3 based polyunsaturated fatty acid.

In addition, increases in blood biochemistry values, urine biochemistry values, pathological changes in pathology concerning conventional renal dysfunction, or indicator A at the time of no protective effect and/or a decrease in index B provide a criterion to suggest that renal function is protected and that the prognosis is favorable.

Accordingly, by using the method for evaluating the effects according to the present invention, a prior prediction of the target effects of administration of n–3 based polyunsaturated fatty acids can be made, allowing for the prediction or confirmation of the effects of n–3 based polyunsaturated fatty acids in prophylactic administration and in coping administration for renal dysfunction and disorders.

For example, even at the stage when renal function is determined to be normal in renal function tests using conventional biomarkers and indices, the presence of at least one change in indices A and B due to administration of n–3 based polyunsaturated fatty acids may predict in advance that renal function will be maintained normally in subsequent administration.

In addition, even when renal function tests using conventional biomarkers and indices cannot confirm the renal function maintenance and renal function protective effects of n–3 polyunsaturated fatty acids, the presence of at least one change in indices A and B due to administration of n–3 based polyunsaturated fatty acids may predict in advance that renal function will be maintained normally in subsequent administration.

According to a prior prediction of the target effects of administration of n–3 based polyunsaturated fatty acids, even for administration targets at risks related to occurrence of renal dysfunction and disorders, it can be predicted in advance that continuous administration of n–3 based polyunsaturated fatty acids can protect renal function and maintain renal function by preventing the occurrence of renal dysfunction and disorders, in the early stage of continuous administration when no renal dysfunction and disorder has occurred.

As shown in Examples described later, administration of the esters of DHA has been found to decrease the concentration of phenylacetic acid in serum in inverse correlation with the increased concentration of N-phenylacetylglycine in the urine, and this result well represents a relationship between the formation of a metabolite by administration of an ester of DHA and its excretion by a glycine conjugate.

Further, according to the method for evaluating an effect according to the present invention, it is also possible to determine an effective dosage of an n−3 based polyunsaturated fatty acid for obtaining an intended effect.

Accordingly, the method for using an n−3 based polyunsaturated fatty acid according to the present invention can have a step of obtaining a dosage of an active ingredient for obtaining an effect evaluated by the above evaluation method, and a step of blending an amount of the active ingredient to be administered into the renal function maintenance and protection agent.

Examples of the administration target of the renal function maintenance and protection agent according to the present invention include mammals including humans in need of maintenance and protection of renal function.

Mammals as non-human animals may include, for example, dogs, cats, mice, rats, rabbits, cattle, horses, monkeys, etc.

Examples of administration targets requiring maintenance and protection of renal function may include mammals, including humans, who are at risk of decreased or impaired renal function due to hypertension, etc.

The renal function maintenance and protection agent according to the present invention can be provided to the administration target in various forms.

For example, the renal function maintenance and protection agent according to the present invention can be provided to the administration target in the form of a food composition containing an n−3 based polyunsaturated fatty acid as an active ingredient, or a pharmaceutical preparation or the like.

Examples of the food composition include foods containing functional foods, additives and food materials used in producing foods containing various processed foods and functional foods, animal feeds, and additives and raw materials used in producing animal feeds.

These various forms can be produced by a method which is usually performed.

An n−3 based polyunsaturated fatty acid having an amount capable of obtaining an intended effect at an appropriate stage of a process for producing can be blended into materials for food or pharmaceutical preparation to produce a renal function maintenance and protection agent in various forms described above.

It should be noted that the food composition as an object of application of the present invention includes all food products, including beverages and includes general processed foods including so-called health foods, health functional foods such as specific health foods or nutritional functional foods defined in the health functional food system of the Japanese Consumer Agency, supplements, and the like, and health functional foods such as specific health foods or nutritional functional foods corresponding in a country other than Japan, supplements, and the like, and further includes feeds to be fed to an animal.

Forms of pharmaceuticals may include oral liquids, tablets, granules, powders, capsules, suppositories, eye drops, jellies, etc.

Also, foods such as functional foods can be provided as, for example, oral liquids, tablets, granules, powders, capsules, jellies, and the like.

Additives such as various carriers, excipients, diluents, and base agents used in pharmaceuticals can be used for formulation as pharmaceutical preparations.

Examples of the additive used in various formulationas include magnesium stearate, talc, lactose, dextrin, starch, methylcellulose, fatty acid glycerides, water, propylene glycol, macrogols, alcohols, crystalline cellulose, hydroxypropylcellulose, low substitution degree hydroxypropylcellulose, carmelloses, popidone, polyvinyl alcohol, and Calcium Stearate.

In this case, if necessary, a colorant, a stabilizing agent, an antioxidant, a preservative, a pH regulator, an isotonizing agent, a dissolution aid and/or an analgesic agent, and the like may be added.

Granules, tablets, or capsules may also be coated with coating bases such as hydroxypropyl methylcellulose, hydroxypropyl methylcellulose phthalate, and the like The content of the n−3 based polyunsaturated fatty acid in these products may be set so as to obtain an intended effect, and is preferably set to be an amount necessary for administration to an application target, for example.

The food to which the present invention can be applied may take a solid, semi-solid or liquid form, and examples of the form to be formulated include various formulation forms such as tablets, pills, capsules, liquids, syrups, powders, granules, and the like The product form of the food composition to which the present invention can be applied, for example, beverages (soft beverages, tea beverages, coffee beverages, milk beverages, fruit juice beverages, carbonated beverages, nutritional beverages, powdered beverages, jelly beverages, alcohol beverages, etc.), pans, noodles, rice products, jelly-like foods, sweets (various snacks, baked sweets, cakes, chocolates, gums, candies, tablets, etc.,), soups, dairy products, frozen foods, processed marine products (fish meat sausages, kamaboko, chikuwa hampen, etc.), livestock processing products (hamburg, ham, sausage, winner, cheese, butter, yogurt, raw cream, margarine, fermented milk, etc.), instant foods, supplements, capsules, serial, other processed foods, seasonings and their materials, etc.

The content of the n−3 based polyunsaturated fatty acid in these products may be set so as to obtain an intended effect, and is preferably set to be an amount necessary for administration to an application target, for example.

As a result of investigation by the present inventor based on the above-described method for evaluating the effect, it has been clarified that it is more effective to make DHA-TG essential as an n−3 based polyunsaturated fatty acid which is an active ingredient of a renal function maintenance and a protective agent.

For example, as shown the results in Table 6 in Example 3 to be described later, it was found that DHA-TG acted more effectively than DHA-BE (ethyl esters of docosahexaenoic acid) in the examination by a biomarker in urine newly used in the present invention.

Therefore, in the present invention, DHA-TG and/or EPA-TG is used as an n−3 based polyunsaturated fatty acid which is an active ingredient of a renal function maintenance and protection agent.

The triglycerides have a molecular structure in which a fatty acid is esterified to 3 hydroxyl groups of glycerin, and in the triglycerides of DHA or EPA, at least one of these fatty acids is DHA or EPA.

As the triglycerides, one kind or a mixture of 2 or more kinds of triglycerides having different numbers of DHA or EPA esterified to 1 molecules of Glycerin may be used.

It is also possible to use tridocosahexaenoyl glyceride (Tri-DHA-TG) in which three DHA molecules are esterified to one glycerin molecule or trieicosapentaenoyl glyceride (Tri-EPA-TG) in which three EPA molecules are esterified.

In addition, at least one of an oil and fat containing at least one of DHA and EPA as triglycerides and a processed product thereof can be used as an active ingredient of a renal function maintenance and protection agent according to the present invention.

Examples of the oil and fat containing at least one of DHA and EPA as triglycerides include fish oil, marine veterinary oil, algal produced lipids, crustacean produced lipids and microbially produced lipids.

Examples of the processed product of oil and fat include concentrates and refined products obtained by enhancing the concentration of triglycerides of at least one of DHA and EPA in oil and fat by at least one of a known concentration method and a purification method.

Oil concentrates or essential oils are preferred concentrates or essential products that contain DHA-TG or EPA-TG alone, or a mixture of DHA-TG and EPA-TG and other fatty acids with concentrations of DHA-TO or EPA-TG between 20 and 95 mass1%. Fatty acids other than DHA and EPA may include palmitic acid, stearic acid and oleic acid.

The renal function maintaining and protective agents according to the present invention can be used for prophylactic administration for maintenance and protection of renal function, and for coping administration for administration subjects with reduced renal function or impaired renal function.

The content of DHA-TG and/or EPA-TO in the renal function maintenance and protection agent according to the present invention may be set so as to obtain an intended effect, and is not particularly limited.

The content of DHA-TG or EPA-TG alone or a mixture of DHA-TG and EPA-TG in the renal function maintenance and protection agents according to the present invention should preferably be set to the amount available for administration (intake) to the target (Ingestion target) at 1000 mg/kg or more per day as DHA or EPA.

In addition, as for the upper limit of the dosage, it is preferable to set the upper limit to 5000 mg/kg or less as DHA or EPA. As for the upper limit of the dosage when a mixture of DHA-TG and EPA-TG is used, it is preferable to set the total amount of DHA and EPA to 5000 mg/kg or less.

The preferred dosage for human adults is 1000 mg/day or more per body as DHA or EPA. In addition, as for the upper limit of the dosage, it is preferable to set the upper limit to 5000 mg/body or less as DHA or EPA. When a mixture of DHA-TG and BPA-TG is used, it is preferable to set the combined amount of DHA and EPA to 5000 mg/body or less as the upper limit of the dosage.

The renal function maintenance and protection agent according to the present invention is preferably administered in a background state of lowering renal function such as bypertension.

The renal function maintenance and protection agent according to the present invention may be provided to a subject for administration together with instructions describing that the effect can be evaluated by the evaluation method described above, or access information to a window, a web site, or the like of a supplier who supplies such information.

EXAMPLE

The present invention will be explained in further detail by examples and the like.

(Example 1) (Study of DHA High-Concentrated Triglyceride Effect)

Spontaneously hypertensive stroke-prone rats (SHR-SP/Izm, Nihon SLC Co., Ltd.) aged 4 weeks were acclimatized for 1 week, then fed an 8-mass % salt-containing solid diet (AlN-93G, Oriental Yeast Co., Ltd.) and a drinking water freely, and once a day, DHA highly enriched triglycerides (H-DHA-TG) (manufactured by Maruha Nichiro Corporation) were administered by gavage in the amounts shown in Table 1.

[Table 1]

TABLE 1

| Compositions of test groups and dosage | | | |
|---|---|---|---|
| | Test groups | | |
| | Soybean oil (mg/kg/day) | H-DHA-TG (mg/kg/day) | DHA content (mg/kg/day) |
| Control | 3,000 | 0 | 0 |
| H-DHA-TG 500 | 2,500 | 500 | 300 |
| H-DHA-TG 1,000 | 2,000 | 1,000 | 600 |
| H-DHA-TG 2,000 | 1,000 | 2,000 | 1,200 |
| H-DHA-TG 3,000 | 0 | 3,000 | 1,800 |

Body weight, food intake and water consumption were measured weekly, and blood pressure was measured by the tail-cuff method before, 2 weeks after and 4 weeks after the start of administration.

In addition, urine samples were collected before the start of administration and after 4 weeks of administration under fasting for 16 hours, and biochemical tests and metabolite analysis by NMR were performed by conventional methods.

At the end of the test, blood was collected from the abdominal vena cava and necropsied.

Biochemical metabolite analysis was performed on the obtained serum by conventional methods.

The kidneys were fixed in formalin solution, followed by PAS-staining and Sirius-Red-staining.

For PAS-staining, along with pathomorphological observations, glomerulosclerosis score (GSI), renal artery injury score (AIS) were performed with reference to Clinical and Experimental Hypertension, 2012, 34 (2) 99-106.

The results obtained are shown in FIGS. 1 to 4, and Table 2.

As shown in FIG. 1, when the H-DHA-TG dose was 500 mg/kg (DHA content of 300 mg/kg) or less group, onsets of stroke and deaths were observed during the test period. On the other hand, when the H-DHA-TG dose was 1,000 mg/kg/day (DHA content of 600 mg/kg) or more group, very few deaths were observed.

As shown in FIG. 2, a dose-dependent increase inhibition effect of H-DHA-TG was observed for blood pressure.

As shown in Table 2, blood and urine chemistry parameters related to renal function showed a remarkable response at the H-DHA-TG dose of 2000 mg/kg or more (DHA content of 1200 mg/kg).

[Table 2]

TABLE 2

Renal function index values

| Items | Control | H-DHA-TG 500 | H-DHA-TG 1000 | H-DHA-TG 2000 | H-DHA-TG 3000 |
|---|---|---|---|---|---|
| Serum BUN (mg/dL) | 24.2 ± 2.8 | 26.5 ± 5.4 | 28.4 ± 5.3 | 25.0 ± 2.8 | 25.5 ± 3.2 |
| Serum CRE (mg/dL) | 0.32 ± 0.1 | 0.33 ± 0.1 | 0.30 ± 0.1 | 0.23 ± 0.03* | 0.25 ± 0.031 |
| Urine TP (mg/16 h) | 27.3 ± 13.5 | 17.1 ± 12.8 | 18.3 ± 16.1 | 2.8 ± 0.3** | 3.3 ± 0.7** |
| Urine Alb (ug/16 h) | 85.5 ± 33.9 | 51.2 ± 53.8 | 56.8 ± 35.7 | 2.0 ± 2.0** | 0.9 ± 0.4** |
| Urine CRE (mg/16 h) | 24.2 ± 2.8 | 26.5 ± 5.4 | 28.4 ± 5.3 | 25.0 ± 2.8** | 25.5 ± 3.2** |
| Urine Alb/CRE | 27.3 ± 12.4 | 15.1 ± 15.9 | 15.9 ± 9.9 | 0.6 ± 0.6** | 0.3 ± 0.1** |
| GSI | 9.4 | 8.5 | 4.8 | 2.4* | 0.9** |
| AIS | 35.3 | 31.7 | 21.7 | 3.1*** | 1.0*** |

Mean ± standard deviation, GSI, AIS are group average.
Dunnett test: Comparison vs. Control: *$p < 0.05$, $p < 0.01$, *$p < 0.001$ As shown in FIG. 3, a pattern was observed that had a positive correlation with the renal function index creatinine clearance and an inverse correlation with the renal damage index GSI, AIS, and Album/Cre.

The concentrations of the following compounds as metabolites in urine were measured by 1H-NMR:

(a) methylamine, (b) N-isovaleroylglycine, (c) N-phenylacetylglycine, (d) trimethylamine-N-oxide, (e) 2-hydroxyisobutyrate, and (f) 2-hydroxyvalarate.

As shown in FIG. 4, there was a significant change (Dunnett test) in the H-DHA-TG 2000 mg/kg dosage group and the 3000 mg/kg dosage group compared with the control group, and a significant change (Tuckey-Kramer test) in the H-DHA-TG 1000 mg/kg dosage group compared with the H-DHA-TO 2000 mg/kg dosage group and the 3,000 mg/kg dosage group were observed.

In FIGS. 3 and 4, the box-whisker upper portion bar indicates the 90th percentile value, the box-whisker upper portion indicates the 75th percentile value, the box inner bar indicates the median value, the box-whisker lower bar indicates the 25th percentile value, and the box-whisker lower bar indicates the 10th percentile value, respectively.

(Example 2) (Synthesis of Tri-DHA-TG)

DHA-EE (purity: 97% by mass) (manufactured by Maruha Nichiro Co., Ltd.) (300 g), Glycerin (23 g), and lipase (trade name: Novozyme 435; Novozyme Co., Ltd.) (30 g) as a form of an immobilized enzyme were mixed, and the mixture was stirred under reduced pressure at 60° C. for 72 hours.

After completion of the stirring, the immobilized enzyme was removed from the mixture by filtration.

Filtration was refined by Silica Gel Column Chromatography (FUJI SILYSIA CHEMICAL LTD.: PSA 100 (trade name). Hexane:Ethyl Acetate=7:1 (volume ratio)) to obtain a triglyceride fraction.

The resulting fraction was distilled off the residual solvent by steam distillation to obtain the desired tridocosahexaenoyl triglyceride (Tri-DHA-TG)

(Example 3) (Activity Comparison of DHA-Bound TG and EE)

Spontaneously hypertensive stroke-prone rats (SHR-SP/Izm, Nihon SLC Co., Ltd.) aged 4 weeks were acclimatized for 1 week, then fed an 8-mass % salt-containing solid diet (AIN-93G) and a drinking water freely, and once a day, DHA highly enriched triglycerides (H-DHA-TG), esters (DHA-EE) used in Example 2, and triglycerides (Tri-DHA-TG) prepared in Example 2 were administered by gavage with the amounts shown in Table 3,

TABLE 3

Dosage in each group

| Test groups | Control | H-DHA-TG 2,000 mg/kg (Test substance A) | DHA-EE 1,303 mg/kg (Test substance B) | Tri-DHA-TG 1,246 mg/kg (Test substance C) |
|---|---|---|---|---|
| DHA morphology | — | Triglyceride | Ester | Triglyceride |
| Negative control substance (Soybean oil) dosage | 3,000 mg/kg | 1,000 mg/kg | 1,697 mg/kg | 1,754 mg/kg |
| DHA dosage (mg/kg) | — | 1154 | 1155 | 1166 |

The fatty acid composition of each administration is also shown in Table 4
[Table 4]

TABLE 4

Fatty acid compositions

| Fatty acid compositions | H-DHA-TG — | DHA-EE — | Tri-DHA-TG — |
|---|---|---|---|
| 14:0 | 0.3% | | |
| 16:0 | 1.2% | | |
| 16:1 | 0.3% | | |
| 18:0 | 0.4% | | |
| 18:1 | 1.2% | | |
| 18:4n − 3 | 0.2% | | |
| 20:0 | 0.6% | | |
| 20:1 | 1.1% | | |
| 20:2n − 6 | 0.2% | | |
| 20:3n − 3 | 0.2% | | |

TABLE 4-continued

| Fatty acid compositions | | | |
|---|---|---|---|
| Fatty acid compositions | H-DHA-TG — | DHA-EE — | Tri-DHA-TG — |
| 20:4n − 6 | 0.8% | 0.7% | 0.6% |
| 20:4n − 3 | 0.3% | 0.4% | 0.4% |
| 20:5n − 3 | 3.8% | 0.6% | 0.6% |
| 21:5n − 3 | 0.5% | 0.6% | 0.6% |
| 22:0 | 0.8% | | |
| 22:1 | 1.6% | | |
| 22:4n − 6 | 0.6% | | |
| 22:5n − 6 | 5.4% | | |
| 22:5n − 3 | 3.1% | | |
| 22:6n − 3 | 69.4% | 97.0% | 97.3% |
| 24:0 | 1.1% | | |
| 24:1 | 2.0% | | |
| Unidentified | 4.8% | 0.7% | 0.5% |
| DHA quantification | 57.7 g/100 g | 88.7 g/100 g | 93.6 g/100 g |
| EPA quantification | 3.1 g/100 g | 0.5 g/100 g | 0.5 g/100 g |

Body weight, food intake and water consumption were measured weekly, and blood pressure was measured by the tail-cuff method before, 2 weeks after and 4 weeks after the start of administration.

In addition, urine samples were collected before the start of administration and after 4 weeks of administration under fasting for 16 hours, and biochemical tests and metabolite analysis by NMR were performed by conventional methods.

At the end of the test, blood was collected from the abdominal vena cava and necropsied.

Biochemical metabolite analysis was performed on the obtained serum by conventional methods.

The kidneys were fixed in formalin solution, and then each staining was performed by PAS-staining, Sirius-Red-staining, and immunostaining for α-SMA, CD68, Desmin, and Kim-1 for pathological observations.

For PAS-staining, along with pathomorphological observations, glomerulosclerosis score (GSI), renal artery injury score (AIS) were performed with reference to Clinical and Experimental Hypertension, 2012, 34 (2) 99-106.

And, the area which was recognized as positive by the immunostaining was calculated.

The results obtained are shown in Tables 2 and 3 and FIG. 5.

[Table 5]

TABLE 5

| Renal function index values | | | | |
|---|---|---|---|---|
| Items Bonding style | Control — | H-DHA-TG Triglyceride | DHA-EE Ethyl ester | Tri-DHA-TG Triglyceride |
| Serum BUN (mg/dL) | 32.2 ± 10.6 | 27.2 ± 4.7 | 25.1 ± 3.7 | 25.1 ± 4.2 |

TABLE 5-continued

| Renal function index values | | | | |
|---|---|---|---|---|
| Items Bonding style | Control — | H-DHA-TG Triglyceride | DHA-EE Ethyl ester | Tri-DHA-TG Triglyceride |
| Serum CRE (mg/dL) | 0.40 ± 0.10 | 0.26 ± 0.03*** | 0.28 ± 0.04** | 0.28 ± 0.06*** |
| Urine TP (mg/16 h) | 28.2 | 3.0[†] | 3.2 | 3.2[†] |
| Urine Alb (ug/16 h) | 15532 | 204.4[††] | 1054 | 544.95[†] |
| Urine CRE (mg/16 h) | 2.88 ± 20.7 | 3.40 ± 0.60 | 3.23 ± 0.59 | 3.02 ± 0.47 |
| Urine Alb/CRE | 53.9 | 0.58[††] | 4.44[†] | 1.85[†] |
| GSI | 22.4 | 6.9 | 7.1 | 11.4 |
| AIS | 53.0 | 11.4 | 19.4 | 21.1 |

Mean ± standard deviation, Urine TP, Alb, Alb/CRE show median.

GSI and AIS are group average.

Dunnett test: Comparison vs. Control: *p < 0.05, p < 0.01, *p < 0.001

Steel test: Comparison vs. Control: [†]< 0.05, [††]p < 0.01

[Table 6]

TABLE 6

| Urine metabolic concentration (μM)/Cre(μM) | | | | |
|---|---|---|---|---|
| Items | Control | H-DHA-TG | DHA-EE | Tri-DHA-TG |
| Creatinine | 1.00 ± 0.00 | 1.00 ± 0.00 | 1.00 ± 0.00 | 1.00 ± 0.00 |
| Glycine | 0.11 ± 0.03 | 0.20 ± 0.03** | 0.18 ± 0.04*** | 0.19 ± 0.03** |
| 4-Hydroxyphenylacetate | 0.06 ± 0.00 | 0.11 ± 0.02* | 0.09 ± 0.03 | 0.12 ± 0.04* |
| N-Phenylacetylglycine | 0.24 ± 0.04 | 0.45 ± 0.07* | 0.34 ± 0.09* | 0.42 ± 0.08*** |

Mean ± standard deviation, Dunnett test: Comparison vs. Control: *p < 0.05, p < 0.01, *p < 0.001

As shown in Table 5, both triglycerides and ethyl esters showed an improvement in renal function-related parameters compared with the control group.

As shown in Table 6, we observed that there were more significant differences in triglycerides (H-DHA-TG,Tri-DHA-TG) than in esters (DHA-EE) when the control group was compared with the respective groups.

We also observed that N-phenylacetylglycine and its related metabolite 4-hydroxyphenylacetic acid were significantly excreted in urine in the triglyceride-treated group compared with the control group in correlation with renal function-related indices.

As shown in FIG. 5, on immunostaining, CD68, one of the indices of inflammation, showed more effective inhibition in the TG-group on tissues.

(Example 4) (H-DHA-TG Mechanism of Action and Metabolite Kinetics)

Spontaneously hypertensive stroke-prone rats (SHR-SP/Izm, Nihon SLC Co., Ltd.) aged 4 weeks were acclimatized for 1 week, then fed an 8-mass % salt-containing solid diet (AlN-93G) and a drinking water freely, and once a day, DHA highly enriched triglycerides (H-DHA-TG) (0, 1000, 2000 ml/kg) (manufactured by Maruha Nichiro Corporation) were administered by gavage with the amounts shown in Table 7.

In order to capture the change over time, autopsy of each group and collection of specimens were performed according to the scheme shown in FIG. 6 at the start of the test, 2 weeks after the start of the test, and 4 weeks after the start of the test.

[Table 7]

TABLE 7

| | | Dosage in each group | |
| --- | --- | --- | --- |
| Test groups | Control | H-DHA-TG 1,000 mg/kg (Test substance A-1) | H-DHA-TG 2,000 mg/kg (Test substance A-2) |
| Negative control substance (Soybean oil) dosage | 3,000 mg/kg | 2,000 mg/kg | 1,000 mg/kg |
| Number of animals at the start (40 in total) | n = 18 | n = 12 | n = 10 |
| Autopsy time and number of animals   0 w | n = 5 | — | — |
|   2 w | n = 5 | n = 5 | n = 5 |
|   4 w | n = 8 | n = 7 | n = 5 |

Body weight, food intake and water consumption were measured weekly, blood pressure was measured by the tail-cuff method before, 2 weeks after and 4 weeks after the start of administration, urine samples were collected after 4 weeks of administration under fasting for 16 hours, and biochemical tests and metabolite analysis by NMR were performed by conventional methods.

In addition, blood was collected from the abdominal vena cava according to the test plan, and autopsy was performed.

The obtained serum was used for biochemistry, and metabolite analysis by GC-MS was performed by conventional methods.

Biochemical metabolite analysis was performed on the obtained serum by conventional methods.

The kidneys were fixed in formalin solution, followed by PAS-staining and Sirius-Red-staining.

The kidneys were fixed in formalin solution, and then each staining was performed by PAS-staining, Sirius-Red-staining, and immunostaining for α-SMA, CD68, Desmin, and Kim-1 for pathological observations.

For PAS-staining, along with pathomorphological observations, glomerdosclerosis score (GSI), renal artery injury score (AIS) were performed with reference to Clinical and Experimental Hypertension, 2012, 34(2)99-106.

And, the area which was recognized as positive by the immunostaining was calculated.

The results obtained are shown in Tables 8 to 11 and FIG. 7.

[table 8]

TABLE 8

| | | | | | | | |
| --- | --- | --- | --- | --- | --- | --- | --- |
| | Renal function index values (blood biochemical test * pathological test) | | | | | | |
| | | Test groups | | | | | |
| | | | 2 w | | | 4 w | |
| | 0 w Control | Control | H-DHA-TG 1,000 mg/Kg | H-DHA-TG 2,000 mg/kg | Control | H-DHA-TG 1,000 mg/kg | H-DHA-TG 2,000 mg/kg |
| n | 5 | 5 | 5 | 5 | 2 | 7 | 5 |
| Serum BUN (mg/dL) | 12.2 ± 1.4 | 17.6 ± 1.9 | 18.3 ± 3.0 | 22.9 ± 3.4 | 30.1 ± 13.4 | 23.0 ± 2.5 | 22.9 ± 2.9 |
| Serum CRE (mg/dL) | 0.20 ± 0.02 | 0.23 ± 0.03 | 0.26 ± 0.03 | 0.26 ± 0.06 | 0.35 ± 0.09 | 0.28 ± 0.05 | 0.26 ± 0.03 |
| GSI | 5.0 | 4.0 | 3.4 | 3.8 | 20.5 | 5.9 | 3.2 |
| AIS | 0.6 | 0.0 | 0.4 | 0.2 | 55.1 | 10.1 | 2.2 |

[table 9]

TABLE 9

| | | | | | | | | | |
| --- | --- | --- | --- | --- | --- | --- | --- | --- | --- |
| | Renal function index values (urine biochemical test) | | | | | | | | |
| | | 0 w | | | 2 w | | | 4 w | |
| | Control | H-DHA-TG 1,000 mg/Kg | H-DHA-TG 2,000 mg/kg | Control | H-DHA-TG 1,000 mg/kg | H-DHA-TG 2,000 mg/kg | Control | H-DHA-TG 1,000 mg/kg | H-DHA-TG 2,000 mg/Kg |
| n | 18 | 12 | 10 | 13 | 12 | 10 | 2 | 7 | 5 |
| Udine TP (mg/16 h) | 0.30 ± 0.14 | 0.36 ± 0.17 | 0.34 ± 0.16 | 1.22 ± 0.40 | 1.16 ± 0.33 | 1.14 ± 0.33 | 17.2 ± 9.24 | 6.01 ± 8.77** | 2.45 ± 0.76** |
| Urine Alb (μg/16 h) | 3.06 ± 3.54 | 2.64 ± 1.82 | 2. 60 ± 1.65 | 1.98 ± 1.37 | 2.72 ± 2.76 | 2.33 ± 1.22 | 52.1 ± 39.2 | 22.8 ± 27.1** | 3.65 ± 1.25*** |
| Urine CRE (mg/16 h) | 0.77 ± 0.24 | 0.81 ± 0.29 | 0.71 ± 0.27 | 1.76 ± 0.39 | 1.84 ± 0.41 | 1.81 ± 0.36 | 3.23 ± 0.10 | 2.77 ± 0.58 | 2.61 ± 0.47 |
| Urine Alb/CRE Alb/CRE | 5.39 ± 7.85 | 4.60 ± 4.64 | 10.5 ± 17.9 | 1.25 ± 1.00 | 1.77 ± 2.12 | 16.3 ± 12.7 | 16.3 ± 12.7 | 7.47 ± 7.07 | 1.41 ± 0.43 | table 10]

TABLE 10

| Urine metabolite concentrations (μM)/Cre(μM) | | | | | | | | |
|---|---|---|---|---|---|---|---|---|
| Test groups | | | | | | | | |
| 0 w | | | 2 w | | | 4 w | | |
| Control | H-DHA-TG 1,000 mg/kg | H-DHA-TG 2,000 mg/kg | Control | H-DHA-TG 1,000 mg/kg | H-DHA-TG 2,000 mg/kg | Control | H-DHA-TG 1,000 mg/kg | H-DHA-TG 2,000 mg/kg |
| n | 16 | 10 | 6 | 13 | 12 | 10 | 2 | 7 | 5 |
| Creatinine | 1.00 ± 0.00 | 1.00 ± 0.00 | 1.00 ± 0.00 | 1.00 ± 0.00 | 1.00 ± 0.00 | 1.00 ± 0.00 | 1.00 ± 0.00 | 1.00 ± 0.00 | 1.00 ± 0.00 |
| N-isovaleroyl-glycine | 0.05 ± 0.01 | 0.04 ± 0.01 | 0.04 ± 0.01 | 0.02 ± 0.00 | 0.05 ± 0.01*** | 0.10 ± 0.02*** | 0.02 ± 0.00 | 0.04 ± 0.01 | 0.09 ± 0.01*** |
| N-Phenyl-acetylglycine | 0.25 ± 0.04 | 0.24 ± 0.04 | 0.24 ± 0.04 | 0.30 ± 0.04 | 0.28 ± 0.05 | 0.38 ± 0.06** | 0.23 ± 0.07 | 0.25 ± 0.03 | 0.38 ± 0.06** |
| 1-Methyl-nicotinamide | 0.04 ± 0.01 | 0.04 ± 0.01 | 0.04 ± 0.01 | 0.02 ± 0.00 | 0.02 ± 0.01* | 0.03 ± 0.01*** | 0.01 ± 0.00 | 0.01 ± 0.00 | 0.02 ± 0.00** |
| Nicotinamide N-oxide | 0.01 ± 0.01 | 0.01 ± 0.01 | 0.01 ± 0.01 | 0.00 ± 0.00 | 0.01 ± 0.01* | 0.02 ± 0.01*** | 0.01 ± 0.01 | 0.01 ± 0.00* | 0.02 ± 0.00*** |
| Nicotinurate | 0.03 ± 0.01 | 0.03 ± 0.01 | 0.03 ± 0.01 | 0.02 ± 0.00 | 0.02 ± 0.01 | 0.03 ± 0.01*** | 0.01 ± 0.01 | 0.01 ± 0.00 | 0.02 ± 0.01** |

Dunnett test: vs. Control *p < 0.05, p < 0.01, *p < 0.001

[table 11]

TABLE 11

| Serum metabolite concentrations (relative area volues according to internal standard) | | | | | | | |
|---|---|---|---|---|---|---|---|
| | Test groups | | | | | | |
| | 0 w | 2 w | | | 4 w | | |
| | Control | Control | H-DHA-TG 1,000 mg/kg | H-DHA-TG 2,000 mg/kg | Control | H-DHA-TG 1,000 mg/kg | H-DHA-TG 2,000 mg/kg |
| N | 5 | 5 | 5 | 5 | 2 | 7 | 5 |
| 2-Aminopimelic acid-3TMS | 3.42 ± 0.24 | 3.17 ± 0.49 | 2.86 ± 0.61 | 2.45 ± 0.99** | 3.32 ± 0.60 | 2.40 ± 0.33* | 2.17 ± 1.10* |
| 2-Hydroxybutyric acid-2TMS | 1.93 ± 0.13 | 1.87 ± 0.39 | 1.51 ± 0.43 | 0.03 ± 1.07*** | 1.73 ± 0.29 | 0.82 ± 0.37* | 0.64 ± 0.43** |
| Citric acid-4TMS | 6.02 ± 0.41 | 5.40 ± 0.75 | 5.10 ± 1.09 | 4.50 ± 1.79* | 6.01 ± 0.09 | 4.45 ± 0.06 | 3.86 ± 1.90* |
| Glycolic acid-2TMS | 0.46 ± 0.04 | 0.39 ± 0.04 | 0.35 ± 0.09 | 0.31 ± 0.09** | 0.38 ± 0.04 | 0.30 ± 0.03 | 0.26 ± 0.09* |
| Glycine-3TMS | 110.6 ± 19.7 | 115.1 ± 16.5 | 127.6 ± 41.0 | 144.17 ± 25.5 | 88.0 ± 19.7 | 121.7 ± 24.1** | 136.1 ± 23.0** |
| Phenylacetic acid-TMS | 0.10 ± 0.03 | 0.11 ± 0.03 | 0.05 ± 0.08* | 0.01 ± 0.04** | 0.12 ± 0.03 | 0.06 ± 0.03* | 0.02 ± 0.06*** |
| Niacinamide-TMS | 0.28 ± 0.06 | 0.23 ± 0.11 | 0.34 ± 0.07 | 0.44 ± 0.10** | 0.28 ± 0.12 | 0.28 ± 0.05 | 0.41 ± 0.11 |

Dunnett test: vs. Control *p < 0.05, p < 0.01, *p < 0.001

As shown in Table 8, Table 9, and FIG. 7, no changes in biochemical or pathological renal function indices were observed 2 weeks after administration with or without H-DHA-TG treatment.

On the other hand, at 4 weeks after administration, the same reproduction was observed as in Example 1.

As shown in Table 10, the urinary metabolites N-phenylacetylglycine, N-isovaleroylglycine, 1-methylnicotinamide, nicotinamide N-oxide and nicotinurate showed phenotypic preemptive changes from Week 2 in the H-DHA-TG 2 1000 mg/kg administration group that showed protection of renal function, and significant urinary excretion was observed compared with the group that did not exhibit renoprotection.

As shown in Table 11, the serum metabolites 2-aminopimelic acid, 2-hydroxybutyric acid, 3-hydroxybutyric acid, and 3-hydroxyisobutyric acid, citric acid glycolic acid, phenylacetic acid showed phenotypic preemptive changes from Week 2 in the H-DHA-TG administration group that showed protection of renal function, significantly lower values than in the control group was observed, and significantly higher values for niacinamide than in the control group was observed.

The invention claimed is:

1. A method of treating renal function deterioration due to hypertension, the method comprising administering to an administration target who is at risk of renal function deterioration a renal function maintenance and protective agent comprising a triglyceride of docosahexaenoic acid (DHA) or eicosapentaenoic acid (EPA) itself or a mixture of a triglyceride of docosahexaenoic acid (DHA) and a triglyceride of eicosapentaenoic acid (EPA), wherein the renal function maintenance and protective agent is formulated for oral administration.

* * * * *